United States Patent [19]
Frigg

[11] Patent Number: 5,312,403
[45] Date of Patent: May 17, 1994

[54] EXTERNAL FIXATION DEVICE

[75] Inventor: Robert Frigg, Davos, Switzerland

[73] Assignee: Synthes (U.S.A.), Paoli, Pa.

[21] Appl. No.: 917,780

[22] Filed: Jul. 21, 1992

Related U.S. Application Data

[63] Continuation-in-part of Ser. No. 695,390, May 3, 1991, abandoned.

[51] Int. Cl.$^5$ .......................... A61B 17/56; A61F 5/00
[52] U.S. Cl. .......................................... 606/54; 606/86
[58] Field of Search .................. 81/300, 315, 358, 321, 81/324, 326, 415, 416, 417, 418, 219, 318–327; 606/86–88, 157, 152, 205–208

[56] References Cited

U.S. PATENT DOCUMENTS

| | | | |
|---|---|---|---|
| 641,036 | 1/1900 | Pilling | 606/208 |
| 1,420,795 | 6/1922 | Ward | 81/326 |
| 1,635,137 | 7/1927 | Mullens | 606/86 |
| 1,684,775 | 9/1928 | Neikirk | 81/326 |
| 2,240,946 | 5/1941 | Vido | 81/416 |
| 2,427,128 | 9/1947 | Ettinger . | |
| 2,631,585 | 3/1953 | Siebrandt . | |
| 3,013,456 | 12/1961 | Ericson | 81/319 |
| 3,750,652 | 8/1973 | Sherwin | 606/90 |
| 3,840,014 | 10/1974 | Ling | 606/90 |
| 4,475,544 | 10/1984 | Reis | 606/86 |
| 4,572,179 | 2/1986 | Teitelbaum | 606/207 |
| 4,719,827 | 1/1988 | Igarashi | 81/417 |
| 4,724,729 | 2/1988 | Oetiker | 81/415 |
| 4,944,739 | 7/1990 | Torre | 606/53 |
| 5,052,252 | 10/1991 | Szymber | 81/318 |

FOREIGN PATENT DOCUMENTS

752676 9/1933 France .

*Primary Examiner*—Michael A. Brown
*Attorney, Agent, or Firm*—Davis Hoxie Faithfull & Hapgood

[57] ABSTRACT

A bone gripping pincers for osteosynthetic purposes has a swivel joint (1) that can be locked, a minimum of two jaws (2, 3) and a minimum of two legs (4, 5). After bone fragments have been set by means of the bone gripping pincers, its swivel joint (1) can be locked, so that it can act as a permanent bone clamp. The legs (4, 5) can be removed. By a connection pin (9) mounted on the pincers, it is possible to combine several bone pincers into a stable osteosynthetic setting device.

16 Claims, 6 Drawing Sheets

EXTERNAL FIXATION DEVICE

This is a continuation-in-part of copending application Ser. No. 07/695,390 filed on May 3, 1991 now abandoned.

FIELD OF THE INVENTION

This invention relates to a pincers for orthopedic purposes and in particular to a bone gripping pincers having jaws, legs and a hinge which can be locked to secure the jaws in a desired position. The invention further relates to an osteosynthetic setting device comprising a plurality of such pincers joined to a support bar.

BACKGROUND

For treating broken bones, particularly for setting bones or bone fragments, a number of osteosynthetic devices are available to the surgeon.

In recent years, a trend from conservative to operative surgical fracture treatment has been clearly evident. At the beginning of operative fracture treatment, optimum reconstruction of the fracture was in the foreground. No great attention was paid to the blood supply and the soft parts around the fracture. Efforts were made to achieve total stability without consideration for biology. With the spread of intramedullar nailing, it was recognized that total stability of the fracture is not absolutely necessary. Despite somewhat greater instability of the fracture, the minimally disrupted biology could heal the fracture. This new knowledge was also taken into consideration in other types of osteosynthesis. In plate osteosynthesis, for example, fewer screws and smaller and shorter plates are used. The same applies to external fixation devices. Instead of huge multi-dimensional structures with interfragment tension bolts, the simple unilateral setting device became accepted.

Despite the "biological" use of the external fixation device, the fracture does not always heal. This means that the fracture must often be treated with a second operation and another osteosynthetic method. The principal reason for complications are the nails or screws that are driven from outside through the skin and the soft tissue into the bone. Along these nails or screws, germs get into the bone, which leads to what is known as a "pintrak infection." If such an infection occurs, the nails or screws must be removed. While the infection is healing, which takes about ten days, the fracture cannot be set by means of an operation. The consequence is that during this period the patient must be immobilized.

In addition to this risk of infection with customary external setting devices, another disadvantage is becoming more apparent. Measurements with doppler lasers, with which the blood circulation in the bone can be clinically measured, have shown that inserting nails or screws causes a considerable disruption in the circulation in the bone. This means that in inserting external fixation devices, nails, or screws, the surgeon is already creating the next stage in the treatment (including the risk of Pintrak infection and ten-day immobilization of the patient for change of procedure). This has negative effects when, because of time factors, or for treatment of damage to soft tissue, the external setting device is temporarily used. In the case of a catastrophe, such as an airplane crash or railroad accident, injured persons must be treated as quickly as possible. For such cases the external setting device is excellent. Here too, however, the above-described problems will arise.

SUMMARY OF THE INVENTION

The foregoing problems are in large measure overcome by the present invention which comprises a bone pincer, comprising a pair of jaws, a pair of legs which may act as handles and a hinge joining the jaws which can be locked with the jaws in various positions. The pincers can be removably attached to a bone with little penetration of the bone, thus minimizing infection. A plurality of the pincers, attached to a bone, may be connected to support rods to provide a stable but easily removable external fixation device.

BRIEF DESCRIPTION OF THE DRAWINGS

The invention will be further described with reference to the accompanying drawings, in which.

DETAILED DESCRIPTION OF THE INVENTION

Figure 1:
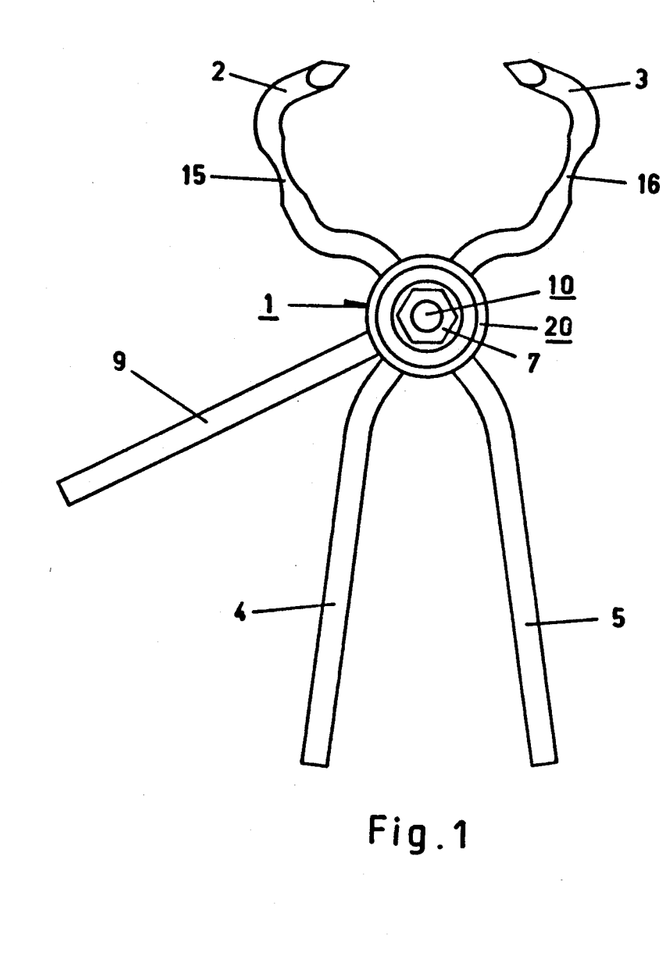
FIG. 1 is a top plan view of an example of pincers according to the invention.

The bone gripping pincers illustrated from above and from below in FIGS. 1 and 2 consists essentially of a hinge or swivel joint 1, a minimum of two jaws 2, 3 and a minimum of two legs 4, 5, which serve as handles. The swivel joint 1 can be operated by manipulation of legs 4, 5, whereby jaws 2, 3 move toward each other. The two jaws 2, 3, bowed like jawbones, may be given a spring-like resilience by narrowing cross-sections 15 or 16, so that when the surgeon grips a bone fragment a manually determined spring force can be exerted. The free ends of the two jaws 2, 3 are sharply pointed, in order to guarantee a secure gripping of the bone fragments.

After the desired bone fragment has been gripped, the swivel joint 1 or its two components, to wit, pin component 10 and bore component 20, can be locked against each other by simple tightening of the nut 7, whereupon the spring tension applied by the surgeon continues and prevents the tension of the pincers from slackening. The swivel joint 1 can be unlocked by a simple unscrewing of the locking nut 7.

Figure 3:
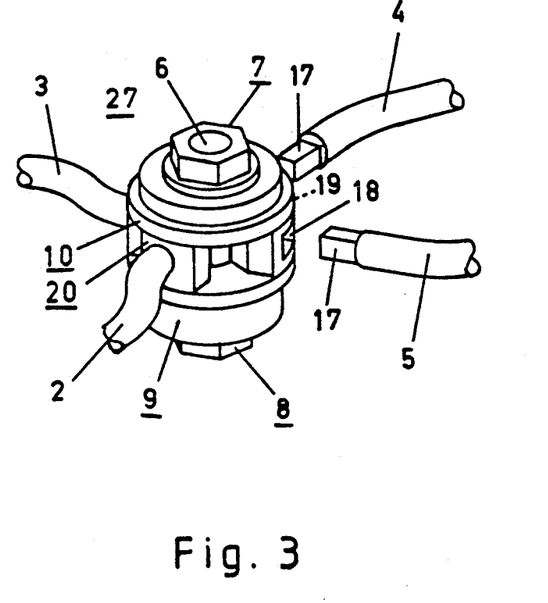
FIG. 3 is a perspective view of the pincers of FIG. 1.

Once the bone gripping pincers has been fixed at the desired position with the desired spring tension, the two legs 4, 5 can be removed from swivel joint 1. For this purpose, as illustrated in FIG. 3, legs 4, 5, are preferably each equipped at the swiveljoint end with a square boss 17 that fits into the corresponding, radially positioned openings 18 (in the swivel bore element 20) and 19 (in swivel pin component 10). This makes it possible to keep the osteosynthetically effective portion of the pincers as small as possible.

Figure 2:
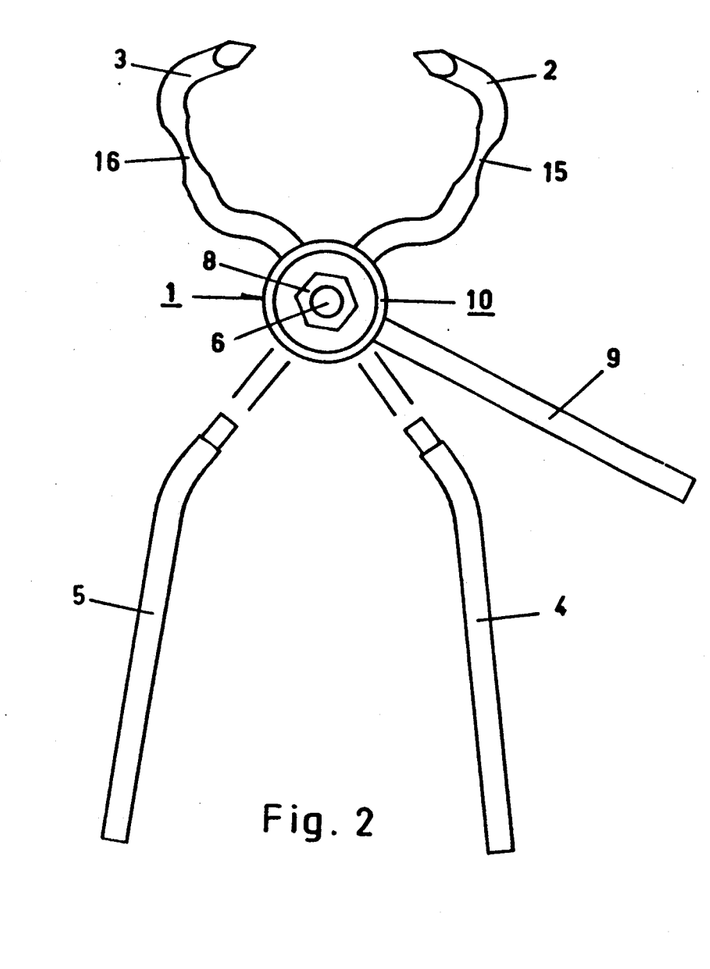
FIG. 2 is a bottom plan view of the pincers of FIG. 1.

As illustrated in FIG. 2, the pincers have a connection pin 9 which can be locked in any desired position by means of a locking nut 8, and which pin is positioned in such manner so that it can be rotated about axis 6 of the swivel pin component 10. This connection pin 9 can be positioned before the operation or during the operation, depending on space conditions. The connection pin 9 makes it possible to connect an entire series of bone gripping pincers together to create a larger assembly. Connecting the pins 9 can be done in conventional manner with the customary aides such as support rods and clamps, as in conventional external fixation systems.

Figure 4:
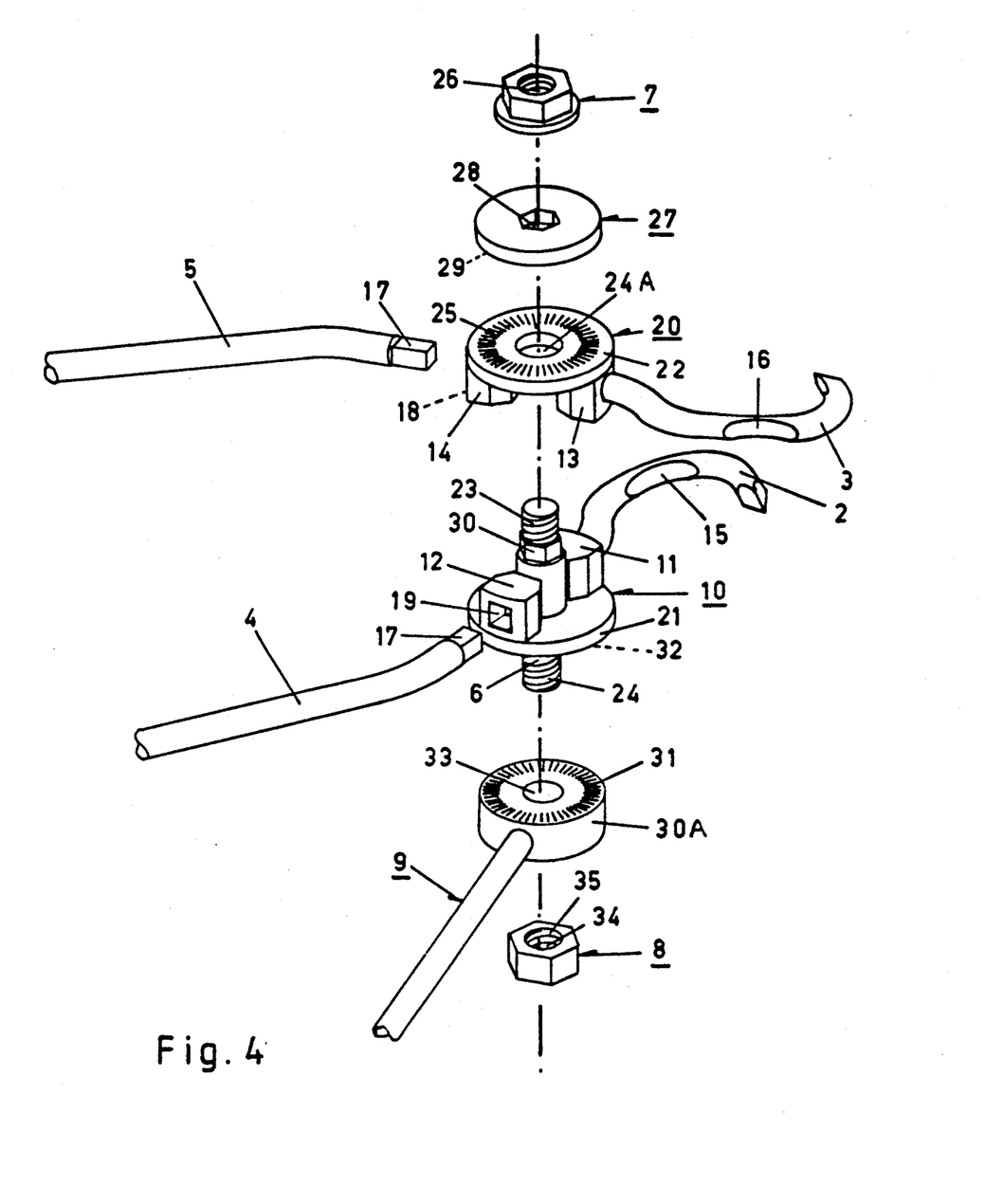
FIG. 4 is an exploded view of the pincers of FIG. 1.

As illustrated in FIG. 4, in one preferred form the swivel joint 1 consists of a pin joint with a pin component 10 and a bore component element 20 for receiving pin component 10. The two elements 10, 20 have disc-shaped bases 21, 22, each of which bears one of the two jaws 2, 3. The base 21 of the pin component 10 has an axially positioned cylindrical pin 6, each of the two ends of which has a thread 23, 24. The base 22 of bore component element 20 has a central bore 24A, designed to receive the cylindrical pin 6.

Each of the two disc-shaped bases 21, 22 has two movement stops (11,12; 13,14), offset concentrically against one another, which limit the rotation of the two components 10, 20 in clockwise and counterclockwise directions.

So that the position of the pin component 10 can be fixed opposite the bore component element 20 in such manner that it can be released, in addition to locking nut 7 with its bore 26 there is a washer 27 between locking nut 7 and bore component element 20, which washer 27 has a hexagonal opening 28 at its center and a concentrically positioned, radially grooved circular area 29 on its underside. The base 22 of bore component element 20 has on its top a radially grooved circular area 25 that corresponds to the circular area 29 of washer 27. Lastly, that portion of swivel pin 6 that is positioned at the level of washer 27 is designed with a hexagonal cross-section 30, which allows washer 27 to rotate when pin 6 is rotated.

When the locking nut 7 is unscrewed, the two components 10 and 20 can move reciprocally (the two grooved circular rings 25, 29 not being in contact with each other); whereas when the locking nut 7 is screwed down the two surfaces 25 and 29 with their ribbed structures are clamped together, so that the washer 27, and hence also the segment 30 of swivel pin 6, which sits tight in the hexagonal opening 28, is locked with respect to the bore component element 20.

By means of a similar construction, it is possible to fix the connection pin 9 in a radial position. For this purpose, the connection pin 9 has a disc-shaped base 30A, which has an annular, grooved zone 31 on its top surface, which zone 31 corresponds with a grooved circular area 32 on the underside of the disc-shaped base 21 of pin component 10.

The disc-shaped base 30A has a centrally positioned bore 33, which can accept the swivel pin 6. By means of the hexagonal nut 8, which has a central bore 34 with internal threading 35, the connection pin 9 can be fixedly connected to the swivel pin 6, the internal threading 35 of bore 34 corresponding to the external thread 24 of pin 6.

If the nut 8 is only partially screwed down on the thread 24, the connection pin 9 can, if desired, be rotated around pin 6; when the nut 8 is screwed tight, the two grooved circular areas 31 and 32 dovetail, so that connection pin 9 can be locked in any desired position.

Figure 5:
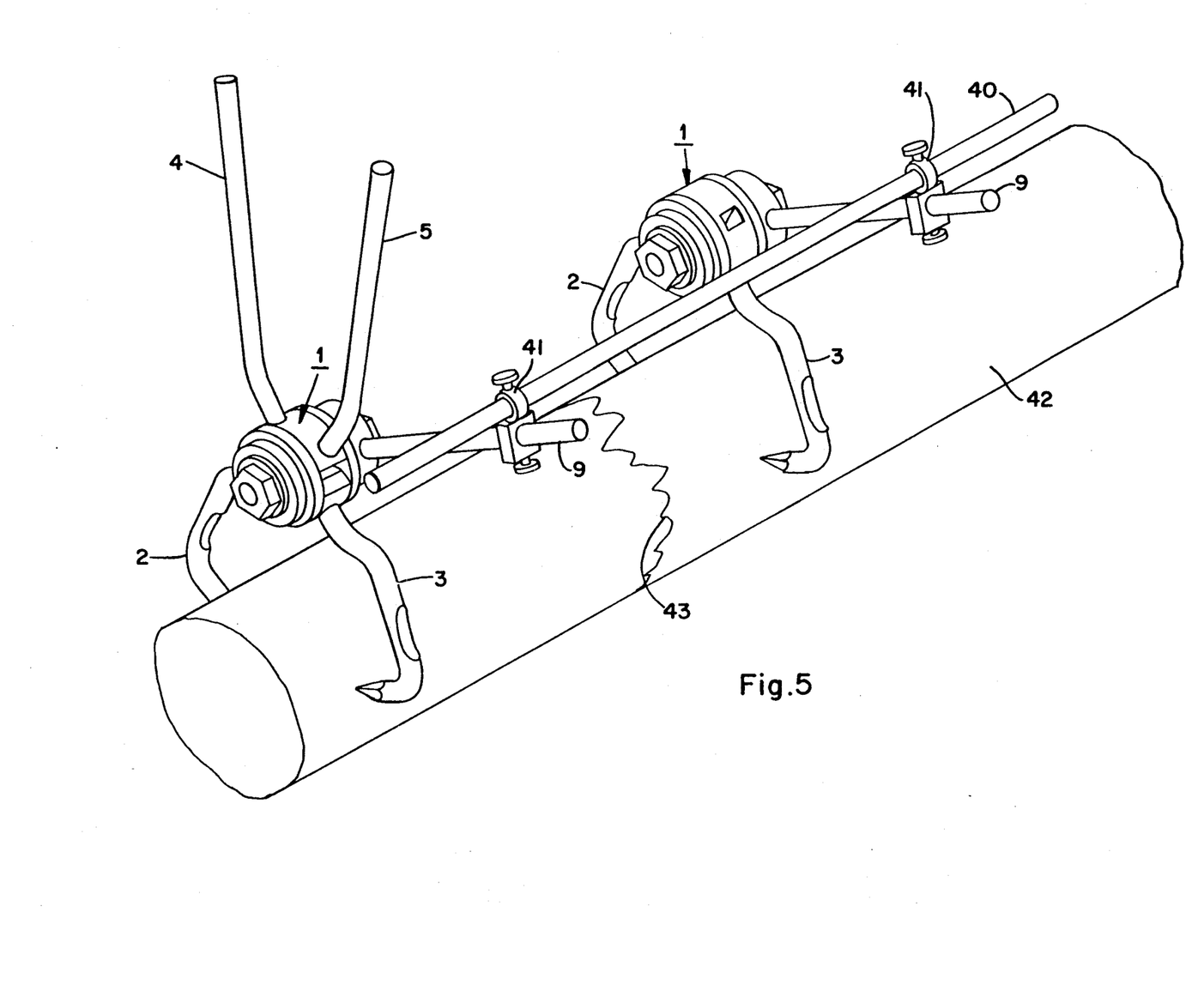
FIG. 5 is a perspective view of an external fixation device using a plurality of the pincers of FIG. 1.

As shown in FIG. 5, thanks to connection pin 9, it is possible to connect two or more bone gripping pincers by means of auxiliary elements (clamps, clips, etc.) to a support rod, to achieve an extremely stable external fixation device. As shown in FIG. 5, two pincers of the type described are connected via their pins 9 and conventional clamps 41 to a support rod 40 on either side of a fracture 43 in a bone 42.

Figure 6:
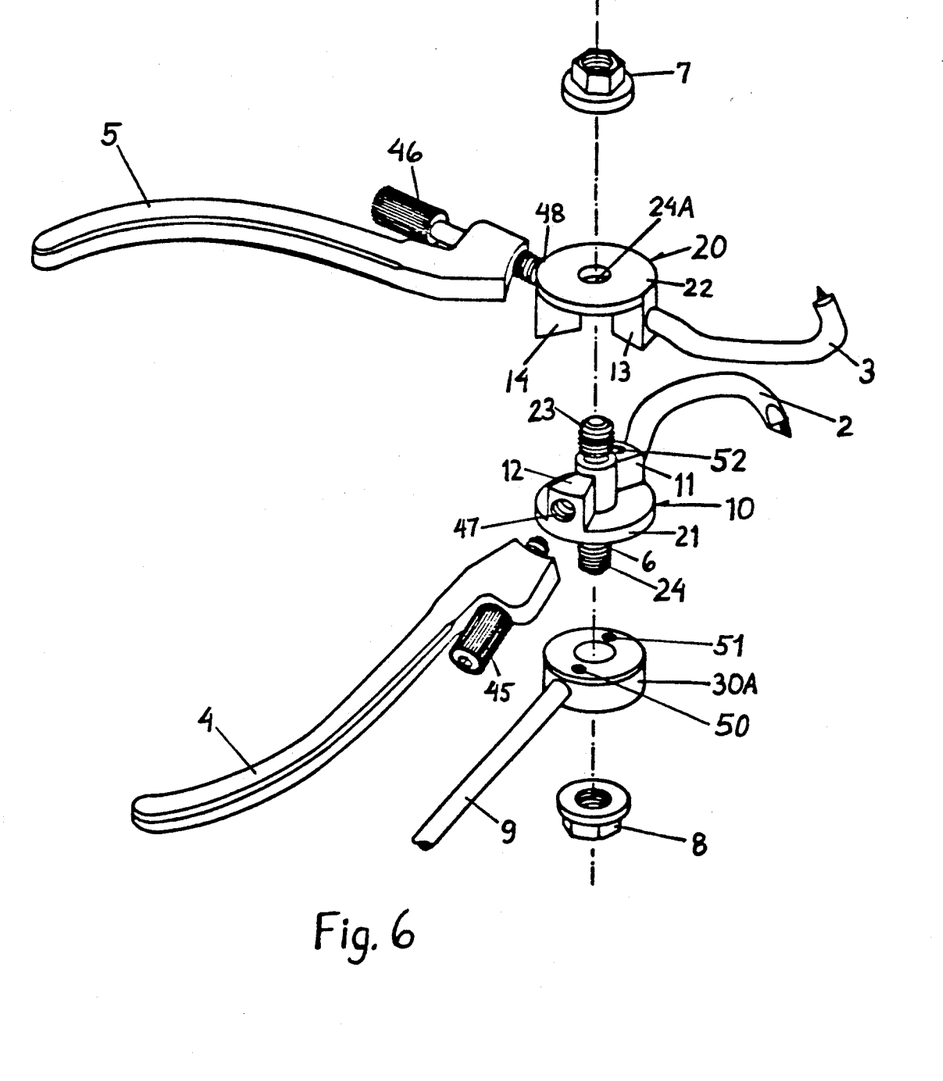
FIG. 6 is an exploded view of an alternate embodiment of the pincers of FIG. 1.

FIG. 6 is an exploded view of an alternate embodiment of the present invention wherein like components are numbered the same as those of FIGS. 1 to 5. The swivel joint consists of a swivel pin component 10 having a disk-shaped base 21, and a bore component 20 having a disc-shaped base 22. The two legs 4, 5 can be attached to, or removed from, the swivel joint by means of set screws 45, 46. The set screw 45 fits into a threaded opening 47 in the swivel pin component 10, and the set screw 46 fits into a threaded opening 48 in bore component 20. One jaw 2 is connected to the swivel pin component 10, and the other jaw 3 is connected to the bore component 20. The base 21 of the pin component 10 has an axially positioned cylindrical pin 6 having threads 23, 24 on its ends, and the base 22 of bore component 20 has a central bore 24A for receiving the cylindrical pin 6. Each of the two disc shaped bases 21, 22 has two movement stops (11, 12; 13, 14), which limit the rotation of the two components 10 and 20 when the components are connected together.

Figure 7:
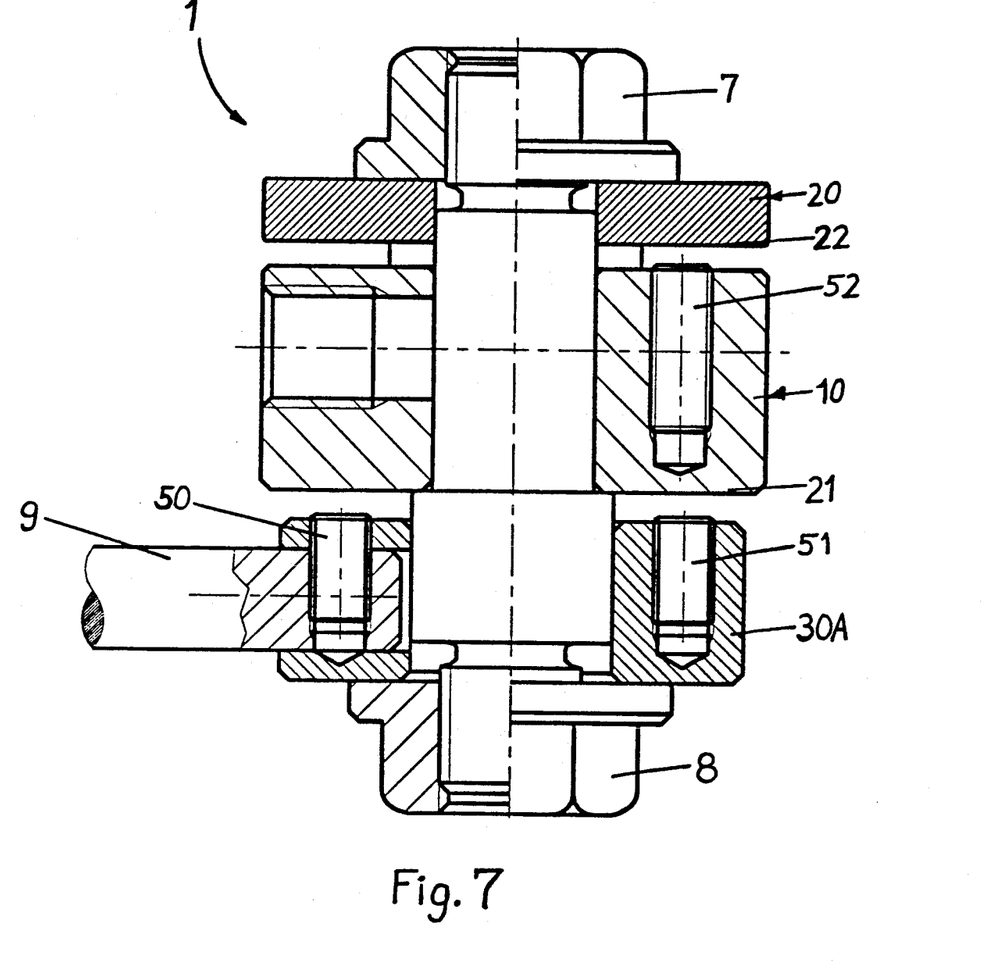
FIG. 7 is an enlarged, cutaway side view of the locking arrangement used with the pincers of FIG. 6.

To lock the jaws 2, 3 in a desired position, locking nuts 7 and 8 are tightened so that the heads of small bolts 50, 51 and 52, depicted in detail in FIG. 7, slightly penetrate the surface opposite their positions. The bolts are seated in the swivel pin component 10 and disc shaped base 30A. When the locking nuts 7 and 8 are tightened, bolts 50 and 51 slightly penetrate the surface of the base 21 of swivel pin component 10, and bolt 52 slightly penetrates the surface of base 22 of bore component 20. This action also fixes the connection pin 9 in place.

FIG. 7 is an enlarged, cutaway side view of the hinge mechanism of FIG. 6. Bolts 50 and 51 are seated in the disc shaped base 30A which supports the connection pin 9, and bolt 52 is seated in the swivel pin component 10. This embodiment of the swivel joint 1 permits a surgeon to lock the hinge at any desired angle. A further advantage of this embodiment is that aluminum may be used to produce the hinge elements.

From the foregoing description, it will be seen that using a device according to the invention, instead of a screw or a nail, the bone is held between the pointed jaws of the bone gripping pincers. The advantage is that no hole need be drilled through the bone, with the result that no heat necrosis is created by the drill and there is minimal disruption of the circulation in the bone. Several such plier-like bone gripping pincers can be externally connected like screws or nails. The principal indication of the bone gripping pincers according to the invention is the temporary setting of open lower-leg fractures. This means that they can be used merely for intra-operative repositioning of the fracture, or they can be left on the bone, after completed repositioning, until the soft parts have completely healed. In both cases there can be a change of procedure (e.g. marrow nailing) with the pincers left in place. Leaving the pincers in place until the fracture has healed poses no problem, though it is seldom appropriate because of the simple possibility of a change of procedure. If a "Pintrak infection" occurs during the treatment period, it is merely superficial and can be treated simply, since the bone under the tips of the bone gripping pincers is vital.

The application of the bone gripping pincers according to the invention is not limited merely to the classic "external fixation". It can be used wherever a fracture must be repositioned or a length of bone must be held.

An advantageous application of the bone gripping pincers according to the invention further consists in the temporary locking of a marrow nail, since the application of the bone gripping pincers according to the invention, compared to screws, is easier and faster and can be done without the use of x-rays.

The same applies in indirect repositioning with a distractor. In place of buttressing screws the bone gripping pincers according to the invention can be used, in order to avoid hole drilling in the bone that is not necessary for treatment of the fracture.

The pincers of the invention offers enormous advantages in the treatment of persons injured in war or in catastrophes, where fractures must be treated without large-scale auxiliary equipment, quickly, and in some cases by persons with minimal training. In these situations, the bone gripping pincers according to the invention offers much lower risk of infection, and no additional instruments or machines are needed. Fractures not treated adequately can be corrected and reset without difficulty at a later date.

Local application of the bone gripping pincers according to the invention depends o the structures of the soft parts (blood vessels, nerves, etc.) that surround the bones. In the presence of structures that are endangered, access to the bone, as when an external setting agent is used, must be carefully prepared.

The design of the invention in the form of a pincers has numerous advantages.

The bone gripping pincers according to the invention can be handled by the surgeon like other pincers-type instruments. Thus the surgeon is already familiar with such devices, and knows how to determine the gripping power of the pincers. The properly positioned application of a pincers is much easier than, for example, the proper application of a clamp. The pincers jaws are preferably constructed in such manner that they have a spring quality. The advantage of this is that if the pincers jaws give way or slip slightly on the bone, the pincers will not lose their grip on the bone.

The pincers lock can be activated by a simple tightening of a screw nut. The advantage of this is that after successful attachment of the bone gripping pincers to the bone, the handle can be removed, so that the external construction can be designed as small as possible.

The connection pin, which moves freely in one direction, makes it possible to connect several individually positioned pincers to a straight connection rod.

The above described embodiments are meant to be merely illustrative of the present invention and are not to be construed as limitations thereof. Thus, a pinless external fixation device according to the present invention covers all modifications, changes and alternatives in its design and construction which come within the scope of the principles taught.

What is claimed is:

1. Pincers for gripping bones for surgical purposes comprising:
   at least two jaws;
   a lockable hinge pivotally joining said jaws to one another, said hinge constituting a swivel joint having a swivel pin component and a bore component, whereby said swivel pin component and said bore component are rotatively but not linearly movable with respect to each other;
   at least two legs, connected to said hinge for pivoting said jaws relative to one another; and
   a removable locking device at said hinge for fixing the pivotal positive of the swivel pin component and the bore component relative to one another.

2. The pincers claimed in claim 1, wherein the jaws have a spring-like resilience.

3. The pincers claimed in claim 1, wherein the legs are removably mounted on the hinge.

4. The pincers claimed in claim 1, wherein the ends of said jaws have sharp tips.

5. The pincers claimed in claim 1, wherein the swivel pin component has a central pin.

6. The pincers claimed in claim 1, and having not more than two jaws and two legs.

7. Pincers for gripping bones for surgical purposes comprising:
   two jaws;
   a swivel joint connecting said jaws to one another, said swivel joint comprising a pin component and a bore component, said bore component being connected to one jaw and said pin component to another jaw, and said swivel pin component and said bore component each having two concentrically offset stops for limiting reciprocal rotation of said components;
   two legs, one connected to each of said pin and bore components for swinging said jaws about said swivel joint; and
   means at said swivel joint for locking said swivel joint to prevent swinging movement of said jaws.

8. Pincers for gripping bones for surgical purposes comprising:
   at least two jaws;
   a lockable hinge joining said jaws to one another, said hinge constituting a swivel joint having a swivel pin component and a bore component, said swivel pin component and said bore component each having two concentrically offset stops for limiting reciprocal rotation of said components;
   at least two legs, connected to said hinge for pivoting said jaws relative to one another; and
   a removable locking device for fixing the positions of the swivel pin component and the bore component relative to one another.

9. Pincers for gripping bones for surgical purposes comprising:
   at least two jaws;
   a lockable hinge joining said jaws to one another, said hinge constituting a swivel joint having a swivel pin component and a bore component, said swivel pin component having a central pin;
   at least two legs, connected to said hinge for pivoting said jaws relative to one another;
   a removable locking device for fixing the position of the swivel pin component and the bore component relative to one another;
   a connection pin; and
   an attachment device for locking the connection pin in any desired position, said connection pin being positioned to rotate on the central pin of the swivel pin component.

10. Osteosynthetic attachment device comprising at least two bone gripping pincers according to claim 9, a support rod and means connecting the connection pins of said pincers to said support rod.

11. Pincers for gripping bones for surgical purposes comprising:

at least two jaws;

a lockable hinge pivotally joining said jaws to one another, said hinge constituting a swivel joint having a swivel pin component and a bore component, whereby said swivel pin component and said bore component are rotatively but not linearly movable with respect to each other;

at least two legs connected to said hinge for pivoting said jaws relative to one another; and a removable locking device for compressing the swivel pin component and the bore component to fix the position of the jaws.

12. The pincers of claim 11, wherein the legs are removably mounted on the hinge.

13. The pincers of claim 11, wherein the ends of the jaws have sharp tips.

14. The pincers of claim 11, wherein the swivel pin component has a central pin.

15. The pincers of claim 11, wherein the removable locking device comprises bolts positioned to slightly penetrate the surface of the swivel pin component and the bore component to lock the hinge.

16. The pincers of claim 11, wherein said removable locking device is at the swivel joint.

* * * * *